(12) United States Patent
Ljusberg-Wahren et al.

(10) Patent No.: US 6,599,517 B1
(45) Date of Patent: Jul. 29, 2003

(54) BONE TISSUE RESTORING COMPOSITION

(75) Inventors: Helena Ljusberg-Wahren, Höllviken (SE); Nils Danielsen, Genarp (SE)

(73) Assignee: Camarus AB, Malmö (SE)

( * ) Notice: Subject to any disclaimer, the term of this patent is extended or adjusted under 35 U.S.C. 154(b) by 0 days.

(21) Appl. No.: 09/743,319

(22) PCT Filed: Jul. 6, 1999

(86) PCT No.: PCT/SE99/01232

§ 371 (c)(1),
(2), (4) Date: Apr. 16, 2001

(87) PCT Pub. No.: WO00/02597

PCT Pub. Date: Jan. 20, 2000

(30) Foreign Application Priority Data

Jul. 13, 1998 (SE) .............................. 9802528

(51) Int. Cl.⁷ ................................. A61F 2/28
(52) U.S. Cl. ...................... 424/423; 424/422; 424/450; 623/16
(58) Field of Search ................. 424/422–428, 424/450, 602

(56) References Cited

U.S. PATENT DOCUMENTS

| 4,192,021 A | | 3/1980 | Deibig et al. .................... 3/1.9 |
| 5,338,772 A | | 8/1994 | Bauer et al. ................. 523/115 |
| 5,807,573 A | * | 9/1998 | Ljusberg-Wahren |

FOREIGN PATENT DOCUMENTS

EP   0 429 419   5/1991

OTHER PUBLICATIONS

"Osteogenesis in Bone Defects in Rats: The Effects of Hydroxyapatite and Demineralized Bone Matrix", Glenn Alper et al., *American Journal of the Medical Sciences*, vol. 298, No. 6, Dec. 1989, pp. 371 to 376. (Discussed at p. 2).
Japanese Patent No. 2,198,560 with English abstract. (Discussed at p. 3).
"Liposomes–Coated Hydroxyapatite and Tricalcium Phosphate Implanted in the Mandibular Bony Defect of Miniature Swine", Jung–Sheng Huang et al., *Kao Hsiung I Koohsiung J. Med. Sci.*, vol. 13, pp. 213–228, 1997. (Discussed at pp. 2 and 3).
Synthesis of Antibiotic–Loaded Hydroxyapatite Beads and in vitro Drug Release Testing, *Journal of Biomedical Materials Research*, vol. 26, pp. 1053–1064, (1992), John Wiley & Sons, Inc. (Discussed at p. 3).
"Calcium Hydroxyapatite Ceramic Used As a Delivery System for Antibiotics", Yoshitaka Shinto et al., *J. Bone Joint Surg*, vol. 74, pp. 600 to 604 (1992), British Editorial Society of Bone and Joint Surgery. (Discussed at p. 3).
Copy of International Search Report dated Oct. 22, 1999.

* cited by examiner

*Primary Examiner*—Gollamudi S. Kishore
(74) *Attorney, Agent, or Firm*—Burns, Doane, Swecker & Mathis, LLP

(57) ABSTRACT

A composition suitable for restoring bone tissue in a human or animal body, which comprises a solid, preferably particulate, calcium phosphate as a biocompatible bone tissue substitute material distributed in a lamellar liquid crystalline phase comprising at least one phospholipid and water or other aqueous liquid as a bioacceptable carrier therefor, said lamellar crystalline phase being pre-formed or being formed in situ in said body in the presence of said water or other aqueous liquid, e.g., body fluid.

40 Claims, No Drawings

BONE TISSUE RESTORING COMPOSITION

This application is a 371 of PCT/SE 99/01232 filed on Jul. 6, 1999.

TECHNICAL FIELD

The present invention relates to the field of implant materials for restoring bone tissues in humans or animals. More specifically the invention relates to a new, easily and consistently applicable composition suitable for restoring bone tissue in a human or animal body, to a method of preparing said composition, to uses of the same as well as to an implant product obtainable from said composition.

BACKGROUND OF THE INVENTION

The repair and reconstruction of osseous defects have long been a serious challenge to the skills of orthopedic and maxillofacial surgeons.

In order to restore form and function to patients, repairing bone defects presently involves several surgical techniques. However, although effective in many cases, the existing technology has numerous difficulties and disadvantages.

Therefore the implantation of materials of different types in the human or animal body in order to replace bone portions which have been traumatized or which have deteriorated due to diseases is steadily increasing. In order to eliminate the risk of having immunological or infectious diseases and to avoid operations on several sites, different synthetic materials have come into use within this technical field. As examples of suitable materials used for said purpose there can be mentioned minerals and ceramics such as tricalcium phosphate and calcium aluminate. Especially preferred materials are, however, materials having a chemical composition and crystal structure similar to those of the materials that are built up by the living organism, such as calcium hydroxy-apatite. One synthetic material of this type which has come into use for restoring bone tissue is the mineral calcium hydroxyapatite and is available both as blocks of different shapes and granules of different sizes.

Commercial hydroxyapatite is supplied by many producers. Thus, for instance, hydroxyapatite of the above-mentioned formula is manufactured by Asahi Optical Co., Ltd., Tokyo, Japan, Interpore Int. Irvine, Calif., USA, and Impladent Ltd., Holliswood, N.Y., USA. The material is available both as resorbable and as non-resorable hydroxyapatite granules/particles for different applications.

In most cases the above-mentioned granules or particles are mixed with blood or a physiological saline solution in order to obtain a mass that is easier to apply to the desired site of the bone, when applying said granules or particles to the bone. A major drawback to this materia or technique is, however, that such a mass is not easily properly confined within the bone cavity referred to. Furthermore, when the mass has been applied to the bone, blood that may come from adjacent bleeding portions of the body or any other secreted body fluid will dilute the particulate mass and may even carry away the material from the site of application.

Attempts to solve these problems have been made, as is for instance disclosed by Alper G. et al. in The American Journal of the Medical Sciences, December 1989 (298): 371–376. However, said reference clearly shows that generally a moldable hydroxyapatite system based on phospholipid and added stearic acid does not stimulate new bone formation or conduct bone growth but rather demonstrates a decrease in bone formation.

Furthermore, since liposomes, which are spherical particles consisting of closed bilayers with water inside as well as outside thereof, have a membrane structure similar to matrix vesicles, Huang et al. have suggested, in Kao Hsiung I Kaohsiung J.Med.Sci. 1997, 13:213–228, that negatively charged liposomes might improve the nucleation process for new bone formation. This concept was tested in a mandibular defect of miniature swine but was not confirmed. Thus, they found that when comparing the bone development of pure calcium phosphate with liposome-coated calcium phosphate the pure implanted material had better and more mature bone tissue development and that the amount of bone tissue was greater than for the implanted material coated with liposomes.

Phospholipids have also been used to produce sustained release formulations of drugs from ceramic granules as is e.g. disclosed in Japanese Patent No. 2,198,560. Antibiotic-loaded hydroxyapatite has been of especial interest since local infections of the operating site is a potential complication. (Df. Yamamura K et al., Journal of Biomedical Materials Research, Vol. 26, 1053–1064 (1992), and Shinto Y. et al., J. Bone Joint Surg., 1992 (74):600–604).

Finally, as concerns implant compositions, reference is also made to EP 0 429 419, which discloses a system where calcium phosphate, and especially hydroxyapatite, is used as a bone tissue substitute material. However, in said case no phospholipid is used but rather a monoglyceride as the basis for the carrier. Furthermore, as in all other cases represented by the prior art, the carrier is not of the same nature as the carrier according to the present invention. Thus, as will be described below the composition according to the present invention as based on a lamellar liquid crystalline phase used as such for the bone formation step. Contrary thereto, EP 0429 419 relies on the use of a phase conversion from an L2-phase into a harder cubic liquid crystalline phase or reversed hexagonal liquid crystalline phase for the bone formation step. In the present case the composition of the lamellar liquid crystalline phase is such that no phase conversion takes place if adding further water. Rather, it is even possible that addition or presence of body fluid after the composition has been implanted promotes the dispersion of the lamellar liquid crystalline phase and the removal of the same from the implant site to thereby enhance the healing process by exposing a bioactive hydroxy-apatite surface to the cells.

The primary object of the present invention is to overcome the drawbacks referred to above and to provide an implant material which can be easily and consistently be applied to the desired site of action, i.e. where the bone tissue restoration is to be made. More specifically, this means that the new implant material according to the present invention is capable of resisting dilution and any forces tending to carry away the material from the place of application.

Furthermore, the bone restoration properties as well as the biocompatibility of the new composition according to the present invention has been found to be outstanding as compared to other, previously known systems.

GENERAL DISCLOSURE OF THE INVENTION

According to the present invention it has been found that the objects referred to above can be achieved by providing a composition wherein a solid calcium phosphate is used as a biocompatible bone tissue substitute material which is distributed in a lamellar liquid crystalline phase comprising at least one phospholipid and water or other aqueous liquid as a bioacceptable carrier therefor. Thus, by using a calcium phosphate, and especially hydroxyapatite, as the main or only bone tissue substitute material in combination with phospholipid(s) in the form of a specific phase, i.e. a lamellar liquid crystalline phase, an implant composition is achieved, the properties of which are outstanding relative to previously known compositions in this field.

In addition to what has been disclosed above concerning advantages of the present invention, it could be added that other previously tested gel systems show several disadvantages. Thus, for instance a water-based gel-like hyaluronic acid is rapidly dehydrated, which means that the consistency thereof varies under the use thereof. This in turn means than it is much more difficult to shape and handle than the composition according to the present invention. The use of proteins like collagen from animals can impart undesirable immunologic reactions, while the use of two component gel systems is a complicated procedure requiring the mixing and curing of two ingredients during a limited time.

Moreover, it should be noted that the composition according to the present invention has been found to show a high amount of newly formed bone while staying very well in the defect tested. Contrary thereto, when using hyaluronic acid as a carrier granules were found outside the tested bone defect, i.e. in soft tissue, where also inflammatory cells were found. It is previously known that particles of calcium phosphate in soft tissue can cause an undesirable cell reaction which does not take place when the granules are present in the bone.

More specifically, the new composition according to the present invention, suitable for restoring bone tissue in a human or animal body, comprises a solid, preferably particulate, calcium phosphate as a biocompatible bone tissue substitute material distributed in a lamellar liquid crystalline phase of at least one phospholipid and water or other aqueous liquid as a bioacceptable carrier therefor, said lamellar liquid crystalline phase being pre-formed or being formed in situ in said body in the presence of said water or other aqueous liquid.

Expressed in another way, the present invention relates to a composition suitable for a composition suitable for restoring bone tissue in a human or animal body, comprising a solid, preferably particulate, calcium phosphate as a biocompatible bone tissue substitute material distributed in a bioacceptable carrier therefor, wherein said bioacceptable carrier comprises at least one phospholipid and water or other aqueous liquid, e.g. body fluid, said at least one phospholipid being present in such amount that a lamellar liquid crystalline phase is formed when providing said water or other aqueous liquid either in a pre-forming operation outside said body or in situ in said body.

In other words, according to one alternative, the lamellar liquid crystalline phase referred to is preformed before being used in a human or animal body for restoring bone tissue therein. According to another alternative said lamellar liquid crystalline phase is formed in situ in said body in the presence of water or other aqueous liquid. In the latter case said water or other aqueous liquid can be added to the site of reaction in the body or being supplied thereto from the body, i.e. in the form of any body fluid (including blood), or a combination thereof. In connection with these alternatives it should thus be noted that the phospholipid(s) are used in such amount(s) that said lamellar liquid crystalline phase can be formed under the circumstances prevailing in each specific case. That is, the composition to be used in any specific case can easily be taken from a common phase diagram for the ingredients used.

The calcium phosphate used as bone tissue substituted material can be chosen according to known principles concerning biocompatible calcium phosphates. Thus, it may be of the resorbable or the non-resorbable type. However, according to a preferable embodiment of the invention a calcium phosphate is utilized which has a molar ratio of Ca:P of from 1:1 to 2:1, preferably from 1.5:1 to 1.7:1. An especially preferable calcium phosphate of this type is calcium hydroxyapatite, most preferably a hydroxyapatite of the formula $Ca_{10}(PO_4)_6(OH)_2$.

As has been mentioned already above the solid calcium phosphate is preferably used in the form of particles, especially granules, a preferable size thereof being from 0.05 mm to 5 mm, expressed as an average diameter thereof.

The calcium phosphate used in accordance with the present invention can be a porous or dense material. However, it has been found that the use of a porous material instead of a dense one may have certain advantages, e.g. by allowing an ingrowth of bone tissue which seems to lead to a more complete and rapid stabilization of the bone tissue substitute material at the recipient site. An especially preferable porosity in this respect is in the range of 20 to 80%.

As mentioned, the calcium phosphate is the major, or only, bone tissue substitute material of our composition. However, one advantageous embodiment of the invention is represented by the case where the composition also contains natural bone, i.e. of human or animal origin. For obvious reasons such bone is preferably taken from the human being or animal involved in the bone tissue restoring procedure, such as bone granules or particles obtained when e.g. drilling a bone cavity in connection with a bone tissue restoring operation of the type referred to.

Contrary to what is disclosed in prior art it has also been found especially preferable in connection with the present invention to use a phospholipid which is substantially neutral, i.e. non-charged, under physiologically conditions. Expressed in another way this means that in accordance with the present invention the phospholipid is preferable used alone, i.e. for instance without any added stearic acid or other acid compound as in connection with some prior art.

Generally the phospholipid carrier is selected from the group consisting of glycerophospholipids and sfingolipids. The acyl groups of such glycerophospholipids and/or sfingolipids, which groups may be the same or different, are each preferably derived from a saturated or unsaturated fatty acid having 14–22 carbon atoms, especially 16–20 carbon atoms. More preferably said fatty acid is a fatty acid having 16 or 18 carbon atoms, especially an unsaturated (including mono- or polyunsaturation) fatty acid having 18 carbon atoms. Most preferable in this respect is oleic acid and/or linoleic acid, preferably oleic acid.

The phospholipid referred to can of course be an entirely synthetic product but can also be derived from a natural product in the form of a vegetable or animal raw material. Examples of such raw materials are a vegetable oil or egg yolk, such as soy bean oil, rape-seed oil, etc.

Preferred examples of glycerophospholipids are such which are derived from lecitines. Especially preferred is phosphatidylcholine.

An especially preferred sfingolipid is sfingomylein, which is also based on choline. A specific group of phospholipids is diacylphosphatidylcholines.

A further preferable embodiment of the composition claimed is a composition wherein the phospholipid carrier also contains an antioxidant, which can be selected among known antioxidants in accordance with principles known per se. However, an example of an advantageous antioxidant in this respect is tocopherol.

The exact ratios between the ingredients in the composition of the invention are dictated by the fact that a lamellar liquid crystalline phase is to be created and utilized. Therefore, the exact compositions to have the desired phase can easily be determined by a person skilled in the art, for instance by means of a phase diagram for the specific ingredients used. However, preferable embodiments with reference to such compositions are the following.

A preferable weight ratio of calcium phosphate to phospholipid is within the range of 70:15 to 60:40.

The weight ratio of phospholipid to water or other aqueous liquid is generally within the range of 1:2 to 10:1, preferably 3:2 to 4:1

With reference to the aqueous liquid utilized to form the lamellar liquid crystalline phase referred to it can, thus, be water or any other aqueous liquid by means of which said phase can be formed. Preferably pure water, an isotonic salt solution or a pharmaceutically acceptable buffer is utilized, but if advisable for any reasons, e.g. in the case where said phase is formed in situ, any aqueous body fluid, including blood, may be used.

According to a second aspect the present invention also relates to the composition as defined above, also with reference to all preferable embodiments thereof, for use as an implant material composition for restoring bone tissue in a human or animal body.

Furthermore, the invention relates to the use of the above-mentioned composition for the manufacture of a product to be used as an implant material for restoring bone tissue in a human or animal body. All preferable embodiments described above in connection with the implant material composition are equally applicable to this aspect of the invention.

Expressed in another way the invention also relates to a method of restoring bone tissue in a human or animal body, which comprises contacting the composition as defined above with a bone cavity of a human or animal body in need thereof, in order to restore said bone tissue.

Still another aspect of the invention is represented by a method of preparing the above-identified implant material composition. Also in this context all preferable embodiments thereof are included.

Said method comprises either
a) creating said lamellar liquid crystalline phase from said phospholipid(s) and said water or other aqueous liquid and distributing said calcium phosphate bone tissue substitute material therein; or alternatively
b) pre-forming an admixture of said phospholipid(s) and said calcium phosphate bone tissue substitute material in such proportions that said lamellar liquid crystalline phase will be created in situ in the human or animal body when providing said water or other aqueous liquid thereto.

Thus, according to the first alternative the lamellar liquid crystalline phase to be used in accordance with the invention is created outside the body, while according to the second alternative a pre-mixture is formed outside the body, said pre-mixture having such a composition that when used later on for the intended purpose the desired lamellar liquid crystalline phase is created in situ.

As concerns the second alternative referred to the method of restoring bone tissue in a bone of a human or animal body thus comprises applying said pre-mixture to the surface of any bone or bone cavity defect where lost bone tissue is to be restored and allowing said composition to come into contact and/or contacting the same with water or other aqueous liquid in such an amount that the desired lamellar liquid crystalline phase is created.

With reference to the term "distributing" the calcium phosphate bone tissue substitute material in the lamellar liquid crystalline phase, or similar, said term should be interpreted in a broad sense and generally means spreading out in any manner throughout said phase. Expressed in another way the bone tissue substitute material can be said to be dispersed or slurried in the phase referred to.

A preferable embodiment of alternative b) of the method according to the invention is represented by the case where said admixture is formed in the presence of a liquid enabling the manufacture of a sterile lipid solution, which is preferably spread onto said calcium phosphate material, said liquid being then removed by freeze-drying or lyophilization. An example of such a liquid is represented by a lower alkanol, ehtanol being especially preferred.

Finally, the invention also relates to the restored implant bone tissue product per se, i.e. the product which is obtainable by contact between the composition as defined above and body fluid, optionally with added aqueous liquid.

As was mentioned above one major advantage of the present invention is that the new composition is extremely easy to shape and handle and that particles thereof are fully or at least substantially completely prevented from escaping from the application site. Thus, if this would happen, the particles could cause irritation or complication at other places of the body.

Other advantages could be gathered from the present specification or should be obvious to a person skilled in the art after having read the present specification.

In connection with the invention the term "biocompatible" is used, which term has the common meaning that it must not cause any significant side effects in contact with living cells or organisms. Also rheological considerations should be made to make sure that the required phase is adapted for use in contact with the human or animal body, i.e. at temperatures at or around normal body temperature, e.g. at most 40° C.

The use of the composition claimed in the intended implant procedure will follow the general principles in this technical field and need not be described further here.

EXAMPLES

The invention will also be more specifically described by means of the following examples.

Example 1

A lamellar liquid crystalline phase was formed from 21 g of dioleylphosphatidylcholine (Avanti Polar Lipids) and 9 g of a 0.9% by weight saline solution and 70 g of hydroxyapatite granules (Apaceram from Pentax) were added thereto. The composition obtained, designated A, was very easy to shape and handle.

A second composition, designated B, was prepared by dispersing 65% by weight of the hydroxyapatite granules referred to above in a hyaluronic acid carrier (Healon®, Pharmacia & Upjohn, Sweden). Said composition B was not as easy to shape and handle as composition A as it dehydrated rapidly and became crumbly.

The above-identified compositions A and B ware tested in rabbits according to the following protocol.

Animals

Adult New Zealand rabbits of both sexes, weighing 3.5–5.5 kg, were used. The animals were kept 6 weeks post surgery in separate cages and fed with a standard diet and tap water ad libitum.

Surgery

The animals were anaesthetized by i.m. injections of a combination of phentanyl and fluanizone (Hypnorm Vet.®, Janssen Farmaceutica, Denmark) (1 mg/kg body weight) and i.p. injections of diazepam (Apozepam®, Apothekarnes lab. A.S., Norway) (2.5 mg/kg body weight). The animals were shaved and washed with chlorhexidine solution on the lower hind legs before Lidocaine (5% Xylocain®, Astra AB Sweden) was infiltrated subcutaneously to obtain local anesthesia. A careful surgical technique was applied under aseptic conditions, and all hard tissue preparation was performed under generous irrigation with sterile saline (NaCl 9 mg/ml; ACO, Sweden) using a dental handpiece at low speed.

The proximal tibiae was used bilaterally for the bone grafting procedure. After an incision through the skin and periosteum, a flap was raised to expose the bone. The facilitation and standardization of drilling, creation of defects and preparation of transplants were enabled by the use of a drill guide. The guide was applied on the surface of the tibial metaphysis. Two holes (Ø1.8 mm) were drilled through the cortex via the peripheral holes in the drill guide, prethreaded, and titanium marker-screws were inserted (Ø2.0 mm, length 1.5 mm). This procedure allowed the drill guide to be secured in position. Thereafter, a circular defect was made in the tibiae with a trephine drill, Ø4 mm, inserted through the middle hole in the drill guide.

The defects were divided into different groups, two of which received compositions A and B, respectively, and one was left empty (control). The compositions were packed in a syringe and extruded over the defect. Immediately after the grafting procedure the periosteum was repositioned and sutured to prevent bleeding and scattering of the HA particles.

All wounds were closed in three layers: the periosteum and muscle fascia with resorbable polyglactin sutures and the skin with polyamide sutures. Postoperatively, antibiotics (0.1 ml/kg body weight, Intencillin, LEO®, Pharmacia & Upjohn, Sweden) and analgesics (0.05 mg/kg body weight, Temgesic®, Reckitt and Coleman, USA) were administered as single i.m. injections daily for three days.

Preparation of Specimens

The animals were killed after six weeks with an overdose of barbiturate (Mebumal®, ACO Läkemedel AB, Sweden) and fixed by perfusion with 2.5% glutaraldehyde in 0.05 M sodium cacodylate buffer, pH 7.4. The implants and the surrounding bone tissue were removed en bloc, further immersed in glutaraldehyde for 24 hours, and post fixed in 1% osmium-tetroxide for two hours. After dehydration in ethanol, the undecalcified specimens were embedded in plastic resin (LR White, The London Resin Co. Ltd., Hampshire, UK).

The specimens were divided longitudinally by sawing (Exact cutting and grinding equipment, Exact Apparatebau, Norderstedt, Germany) and ground sections of 15–20 $\mu$m (see further in Donath K, Breuner G: A method for the study of undecalcified bones and teeth with attached soft tissues, J Oral Pathol. 11, (1982), 318–326) were prepared and stained with 1% toluidine blue.

Light Microscopy and Morphometry

Light microscopic morphometry was performed on a constant (1003118 $\mu^2$) area centrally placed in the defect.

Morphology

The histological results showed that the HA particles were well accepted when implanted in tibial bone. After 6 weeks new bone was frequently seen in direct contact within the defect, and sometimes on the particles located in the marrow cavity.

The granules appeared to stay well together in the defect in group A (composition according to the invention). However, granules were occasionally observed in the soft tissue directly above the defect when composition B (Healon®) was used as a carrier. No clinical signs of infections were detected in connecetion with composition A while inflammatory cells were found outside the defect, in soft tissue, for composition B.

Morphometry

In comparison with the empty control, the defects grafted with HA particles showed a high amount of newly formed bone in the defects. Thus, the filling of the defect, i.e. granules and new bone, was found to be 63% and 61% in groups A and B, respecticely. This was significantly more than in the control defect, where 13% new bone was formed.

Example 2

Easily shapeable and handleable compositions were prepared from 70.0 g and 69.8 g respectively, of hydroxyapatite granules in 18.0 g and 24.1 g of dioleylphoshatidylcholine, respectively, and 12.0 g and 6.1 g, respectively, of a 0.9% saline solution.

Example 3

30.1 g, 35.1 and 40.0 g of phospholipid (Epikuron ®, Lucas Meyer) were mixed with 69.9 g, 64.9 g and 60.0 g, respectively, of hydroxyapatite granules (Apaceram, Pentax) in the presence of ethanol. After lyophilization of the admixtures obtained shapeable compositions were obtained. The compositions from Examples 2 and 3 can be expected to work similar to compostion A in the tests described in Example 1.

What is claimed is:

1. A composition suitable for restoring bone tissue in a human or animal body, comprising a solid calcium phosphate as a biocompatible bone tissue substitute material distributed in a bioacceptable carrier therefor, wherein said bioacceptable carrier comprises at least one phospholipid present in such amount in an aqueous liquid so as to form a lamellar liquid crystalline phase which does not undergo any phase conversion, said aqueous liquid being present in the composition outside said body or in situ in said body.

2. A composition according to claim 1, wherein said calcium phosphate is a resorbable calcium phosphate.

3. A composition according to claim 1, wherein said calcium phosphate is a non-resorbable calcium phosphate.

4. A composition according to claim 1, wherein said calcium phosphate has a molar ratio of Ca:P of from 1:1 to 2:1.

5. A composition according to claim 4, wherein said calcium phosphate is calcium hydroxyapatite.

6. A composition according to claim 1, wherein said calcium phosphate bone tissue substitute material is in the form of granules thereof.

7. A composition according to claim 1, wherein said calcium phosphate bone tissue substitute material is porous.

8. A composition according to claim 1, wherein said phospholipid is neutral.

9. A composition according to claim 1, wherein said phospholipid carrier is selected from the group consisting of glycerophospholipids and sphingolipids.

10. A composition according to claim 9, wherein the acyl groups of said glycerophospholipids and/or sphingolipids which groups are the same or different, are each derived from a fatty acid having 14–22 carbon atoms.

11. A composition according to claim 10, wherein said fatty acid is a fatty acid having 16 or 18 carbon atoms.

12. A composition according to claim 11, wherein said fatty acid is oleic acid and/or linoleic acid.

13. A composition according to claim 9, wherein said glycerophospholipids is derived from lecithins.

14. A composition according to claim 13, wherein said glycerophospholipid is phosphatidylcholine.

15. A composition according to claim 9, wherein said sphingolipid is sphingomyelin.

16. A composition according to claim 9, wherein said phospholipid is derived from a vegetable oil or egg yolk.

17. A composition according to claim 1, wherein said phospholipid carrier also contains an antioxidant.

18. A composition according to claim 1, wherein the weight ratio of calcium phosphate to phospholipid is within the range of 70:15 to 60:40.

19. A composition according to claim 1, wherein the weight ratio of phospholipid to aqueous liquid is within the range of 1:2 to 10:1.

20. A composition according to claim 1, wherein the bone tissue substitute material is said phosphate in combination with bone of human or animal origin.

21. A composition according to claim 1 for use as an implant material composition for restoring bone tissue in a human or animal body.

22. A method of using a composition according to claim 1 for the manufacture of a product to be used as an implant material for restoring bone tissue in a human or animal body comprising a) forming said lamellar liquid crystalline phase from said phospholipid(s) and said liquid and distributing said calcium phosphate bone tissue substitute material therein; or alternatively b) pre-forming an admixture of said phospholipid(s) and said calcium phosphate bone tissue substitute material in such proportions that said lamellar liquid crystalline phase will be created in situ in the human or animal body when providing said aqueous liquid thereto.

23. A method of preparing a composition suitable for restoring bone tissue in a human or animal body as defined in claim 1, which comprises a) forming said lamellar liquid crystalline phase from said phospholipid(s) and said liquid and distributing said calcium phosphate bone tissue substitute material therein; or alternatively b) pre-forming an admixture of said phospholipid(s) and said calcium phosphate bone tissue substitute material in such proportions that said lamellar liquid crystalline phase will be created in situ in the human or animal body when providing said aqueous liquid thereto.

24. A method according to claim 23, wherein, in alternative b), said admixture is formed in the presence of a liquid enabling the manufacture of a sterile lipid solution, which liquid is then removed by lyophilization.

25. A restored implant bone tissue product obtainable by contact between the composition as defined in claim 1 and body fluid, optionally with added aqueous liquid.

26. A method of restoring bone tissue in a human or animal body, which comprises administering a composition as defined in claim 1 to a bone cavity defect of a human or animal body in need thereof.

27. The composition according to claim 1, wherein said aqueous liquid is selected from the group consisting of water, an isotonic salt solution, a pharmaceutically acceptable buffer and a body fluid.

28. The composition according to claim 1, wherein the calcium phophate is particulate.

29. The method according to claim 24, wherein the liquid is a lower alkanol.

30. The method according to claim 29, wherein the lower alkanol is ethanol.

31. The composition according to claim 4, wherein the calcium phosphate has a molar ratio of Ca:P of from 1.5:1 to 1.7:1.

32. The composition according to claim 5, wherein the calcium hydroxyapatite is of the formula $Ca_{10}(PO_4)_6(OH)_2$.

33. The composition according to claim 6, wherein the granules have a size from 0.05 mm to 5 mm.

34. The composition according to claim 7, wherein the calcium phosphate bone tissue substitute material has a porosity of 20 to 80%.

35. The composition according to claim 10, wherein the fatty acid has 16–20 carbon atoms.

36. The composition according to claim 11, wherein the fatty acid is an unsaturated fatty acid having 18 carbon atoms.

37. The composition according to claim 17, wherein the antioxidant is tocopherol.

38. The composition according to claim 19, wherein the weight ratio of phospholipid to aqueous liquid is 3.2 to 4.1.

39. The composition according to claim 20, wherein the bone is particulate.

40. The composition according to claim 20, wherein the bone is from the same person or animal for whom the bone is being restored.

* * * * *